US009803931B2

(12) United States Patent
Lee

(10) Patent No.: US 9,803,931 B2
(45) Date of Patent: Oct. 31, 2017

(54) HANDPIECE WITH SLIM DRIVING PART OF DIRECT COOLING TYPE

(71) Applicant: MICRO-NX Co., Ltd., Gyeongsangbuk-do (KR)

(72) Inventor: Jong Geon Lee, Daegu (KR)

(73) Assignee: MICRO-NX CO., LTD, Gyeongsangbuk-do (KR)

( * ) Notice: Subject to any disclaimer, the term of this patent is extended or adjusted under 35 U.S.C. 154(b) by 250 days.

(21) Appl. No.: 14/125,471

(22) PCT Filed: Dec. 5, 2012

(86) PCT No.: PCT/KR2012/010446
§ 371 (c)(1),
(2) Date: Dec. 11, 2013

(87) PCT Pub. No.: WO2014/088127
PCT Pub. Date: Jun. 12, 2014

(65) Prior Publication Data
US 2014/0338872 A1 Nov. 20, 2014

(51) Int. Cl.
A61C 1/00 (2006.01)
F28D 7/16 (2006.01)
A61C 1/06 (2006.01)
A61B 17/16 (2006.01)

(52) U.S. Cl.
CPC .......... F28D 7/16 (2013.01); A61C 1/06 (2013.01); A61B 17/1622 (2013.01); A61B 2017/1651 (2013.01); A61C 1/0061 (2013.01)

(58) Field of Classification Search
CPC .......... A61C 1/181; A61C 1/20; A61C 1/052; A61C 1/0007; A61C 1/06; A61C 19/002; A61C 17/24; A61C 17/26

USPC .................................................. 433/103–133
See application file for complete search history.

(56) References Cited

U.S. PATENT DOCUMENTS 4,007,529 A * 2/1977 Fleer ........................ A61C 1/06
433/104
4,184,256 A * 1/1980 Loge ...................... A61C 1/052
433/104
4,547,687 A * 10/1985 Arai ....................... A61C 1/052
310/154.08

(Continued)

OTHER PUBLICATIONS

Translation of KR 101059742 B1—Lee et al./Micro-nx.*

Primary Examiner — Eduardo C Robert
Assistant Examiner — Matthew Saunders
(74) Attorney, Agent, or Firm — Hauptman Ham, LLP

(57) ABSTRACT

The handpiece includes; an outer housing of a bar shape; a cylindrical core inserted into the outer housing and having an air hole and a water hole; pipes respective inserted into the air hole and the water hole of the core; a rotor made with a cylindrical magnetic material and inserted into the core; cylindrical support rings forcedly fit to both sides of transfer shafts of the rotor; a pair of bearings respectively disposed at the front side and the rear side of the support rings; a coupling disposed in front of the rotor; a front housing joined to the front of the outer housing; a front cap disposed at the rear of the core; a rear cap disposed at the rear of the front cap and having a power supply terminal disposed at one side thereof; and a rear housing joined to the rear of the outer housing.

1 Claim, 4 Drawing Sheets

(56) References Cited

U.S. PATENT DOCUMENTS

| | | | | |
|---|---|---|---|---|
| 4,568,283 | A * | 2/1986 | Hotta | A61C 1/08 |
| | | | | 433/104 |
| 8,110,960 | B2 * | 2/2012 | Bischof | H02K 1/20 |
| | | | | 310/216.119 |
| 8,853,895 | B2 * | 10/2014 | Duesing | A61C 1/0061 |
| | | | | 310/50 |
| 2009/0160269 | A1 * | 6/2009 | Bischof | H02K 1/20 |
| | | | | 310/52 |
| 2011/0033823 | A1 * | 2/2011 | Gersh | A61C 17/20 |
| | | | | 433/119 |

* cited by examiner

HANDPIECE WITH SLIM DRIVING PART OF DIRECT COOLING TYPE

CROSS REFERENCE TO RELATED APPLICATION

This application claims the priority of the National Phase application of International Application No. PCT/KR2012/010446 filed Dec. 5, 2012, which designates the United States and was published in Chinese.

BACKGROUND OF THE INVENTION

Field of the Invention

The present invention relates to a handpiece with a slim driving part of a direct cooling type, and more particularly, to a handpiece with a slim driving part of a direct cooling type, in which a pipe for making flow in water and air is joined to a through hole formed in a stator of a motor, thereby effectively cooling heat generated from the motor when the motor in the handpiece is operated.

Background Art

In general, handpieces are mainly used for precision processing, such as dental technique for cutting or polishing teeth in dental clinics, nail art for nail care, jewel processing, and others.

In this instance, the handpiece includes a high speed motor which receives power supply and operates at 50,000 rpm, and when the high speed motor is operated, excessive heat is consequentially generated.

In order to cool the heat generated by the high speed motor, one of a method of injecting saline solution, a method of using electricity, and a method of using air has been used conventionally.

However, the conventional method of injecting saline solution has several problems in that it is less effective in cooling heat of the high speed motor because a pipe for supplying saline solution is formed on the outer face of the stator and indirectly cools the heat generated from the high speed motor and in that saline solution must be continuously injected. The conventional method of using electricity also has several problems in that it is complicated in structure and in that it has bad effect in cooling the heat generated from the high speed motor.

Moreover, the conventional method of using air also has a problem in that it cools only a space around a rotating impeller but does not cool the inside of the handpiece and the whole high speed motor because a flow of air is not good.

Therefore, the conventional methods cannot effectively cool the heat generated from the high speed motor and generate vibration and noise when the high speed motor of the handpiece is operated.

SUMMARY OF THE INVENTION

Accordingly, the present invention has been made to solve the above-mentioned problems occurring in the prior arts, and it is an object of the present invention to provide a handpiece with a slim driving part of a direct cooling type which can effectively cool heat generated from a motor when the motor inside the handpiece is operated and prevent reduction of the lifespan of the motor and generation of vibration and noise due to overheating of the motor.

To accomplish the above object, according to the present invention, there is provided a handpiece with a slim driving part of a direct cooling type including: an outer housing formed in a bar shape and being capable of being grasped by the hand; a cylindrical core inserted into the outer housing and perforated from the front to the rear, the cylindrical core including a coil wound on the inner circumferential surface thereof and an air hole and a water hole respectively perforated from one side of the front portion to one side of the rear portion; cylindrical pipes respectively inserted into the air hole and the water hole of the core and perforated for passing air and water through the pipes, both ends of the pipes respectively protruding forward and backward through the air hole and the water hole; a cylindrical rotor inserted into the core and made with a magnetic material, the cylindrical rotor including transfer shafts respectively extending forward and backward; cylindrical support rings respectively forcedly fit to both sides of the transfer shafts of the rotor in such a manner that one side of each support ring toward the rotor comes in contact with the rotor and the other side is formed protrudingly; a pair of bearings respectively disposed at the front side and the rear side of the support rings and forcedly fit to the transfer shafts so as to rotatably support the rotor; a coupling disposed in front of the rotor and joined to the transfer shaft; a front housing joined to the front of the outer housing and penetrated from the front to the rear such that the transfer shafts and the coupling are inserted into the front housing, the front housing including an air jet hole and a water jet hole respectively formed in the outer circumference thereof for jetting air and water supplied from the pipes; a front cap disposed at the rear of the core, the front cap including: a recess opened toward the front such that the bearing located at the rear of the rotor is inserted into the recess; and a plurality of through holes penetrated from the front to the rear and spaced apart from the recess; a rear cap disposed at the rear of the front cap, the rear cap including: a plurality of through holes formed from the front to the rear corresponding to the through holes of the front cap; and a power supply terminal spaced apart from the through holes and disposed at one side thereof for supplying electric current to the core; and a rear housing joined to the rear of the outer housing for relaying supply of electric current, air and water from the outside.

As described above, because the pipe for making flow in water and air is joined to the through hole formed in the stator of the motor, the handpiece with the slim driving part of the direct cooling type according to the exemplary embodiment of the present invention can effectively cool the heat generated from the motor due to the pipe joined to the stator of the motor, such that the handpiece can prevent reduction of the lifespan of the motor and generation of vibration and noise from the motor by preventing overheating of the motor.

Furthermore, because the pipes are directly inserted into the air hole and the water hole of the core, compared with the conventional handpiece having the pipes disposed on the outer face of the core 10, the handpiece according to the preferred embodiment of the present invention can secure a wider space and become small-sized and slim due to the secured space and can effectively cool the heat generated when the core and the rotor are operated.

In the meantime, the motor which is mainly mounted in the dental handpiece is operated at 50,000 rpm but the pipe joined to the stator of the motor effectively cools the inside heat of the motor, and so, a dentist does not feel displeasure or anxiety due to heat of the motor because the heat is not transferred to the dentist's hand.

BRIEF DESCRIPTION OF THE DRAWINGS

The above and other objects, features and advantages of the present invention will be apparent from the following

DETAILED DESCRIPTION OF THE PREFERRED EMBODIMENT

Reference will be now made in detail to the preferred embodiment of the present invention with reference to the attached drawings.

Figure 1:
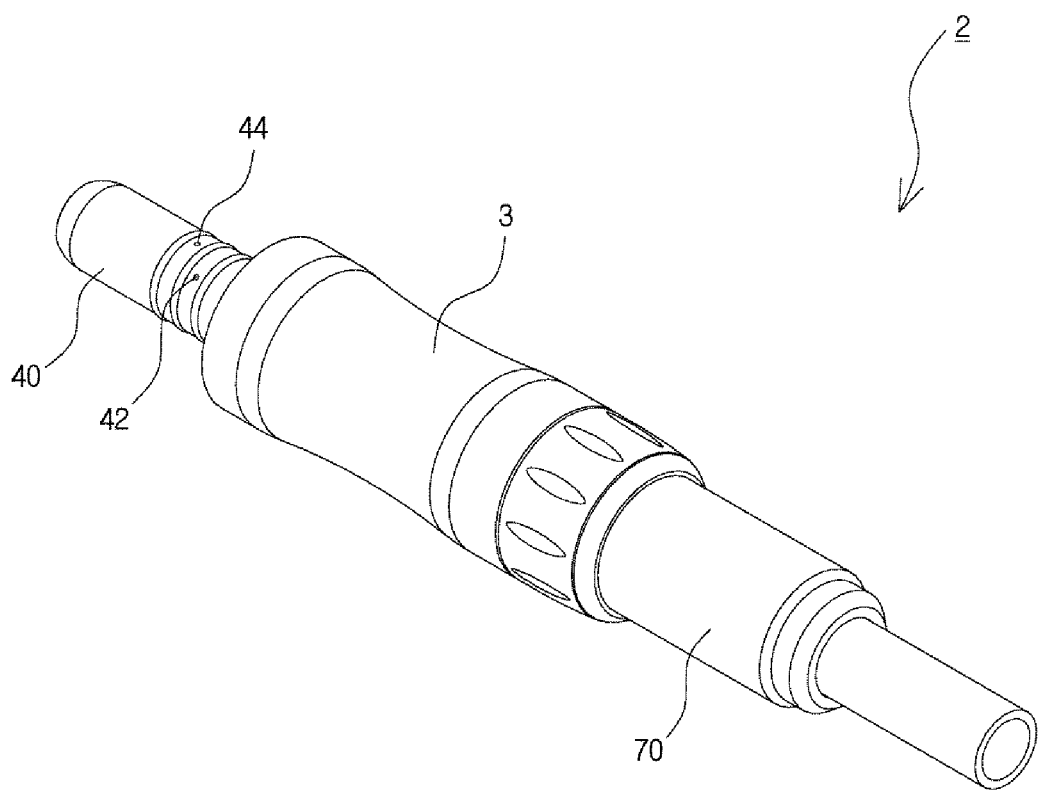
FIG. 1 is a perspective view of a handpiece with a slim driving part of a direct cooling type according to a preferred embodiment of the present invention.
Figure 2:
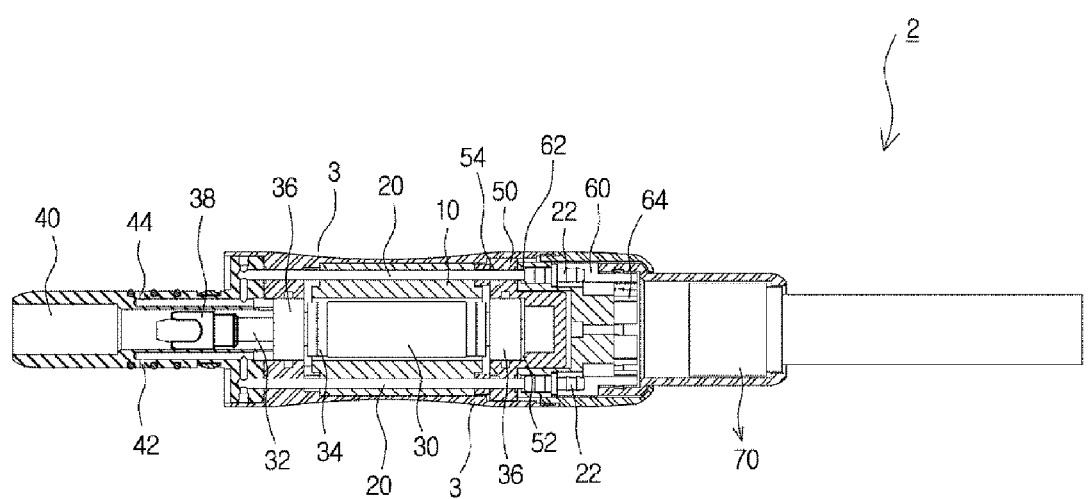
FIG. 2 is a sectional view of the handpiece with the slim driving part of the direct cooling type.
Figure 3:
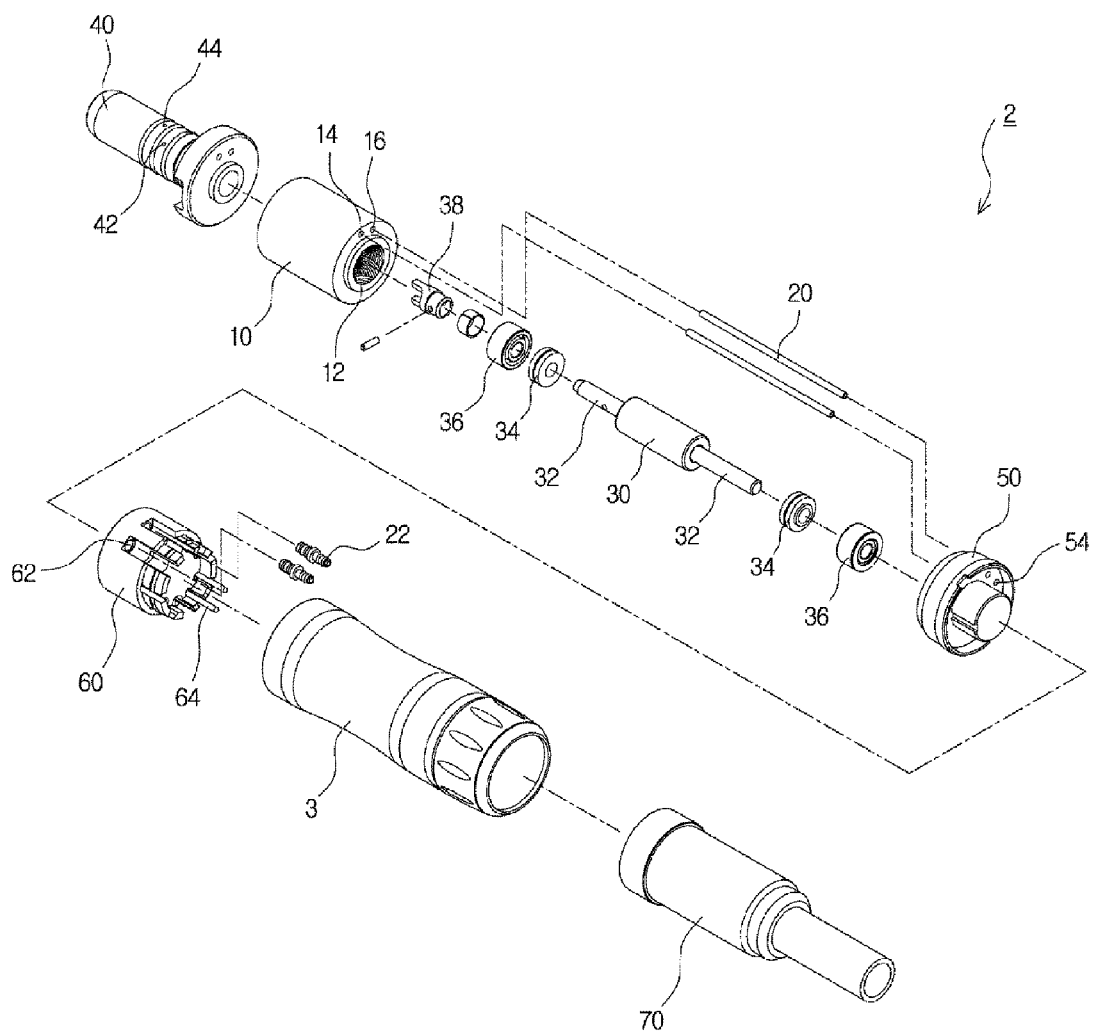
FIG. 3 is an exploded perspective view of the handpiece with the slim driving part of the direct cooling type.
Figure 4:
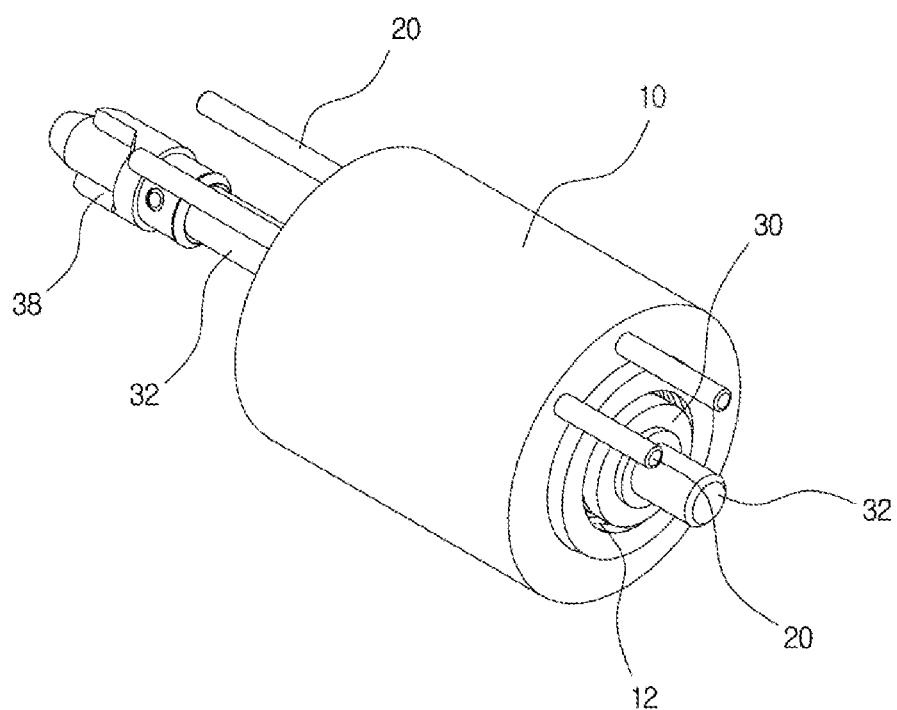
FIG. 4 is a perspective view showing a state where a pipe is joined to a core of the handpiece with the slim driving part of the direct cooling type.

Referring to FIGS. 1 to 4, a handpiece with a slim driving part of a direct cooling type includes: an outer housing 3 of a bar shape constructed in such a way as to be grasped by a user's hand; a cylindrical core 10 inserted into the outer housing 3 and having an air hole 14 and a water hole 16 perforated therethrough; pipes respective inserted into the air hole 14 and the water hole 16 of the core 10; a rotor 30 made with a cylindrical magnetic material and inserted into the core; cylindrical support rings 34 respectively forcedly fit to both sides of transfer shafts 32 of the rotor 30; a pair of bearings 36 respectively disposed at the front side and the rear side of the support rings 34; a coupling 38 disposed in front of the rotor 30; a front housing 40 joined to the front of the outer housing 3; a front cap 50 disposed at the rear of the core 10; a rear cap 60 disposed at the rear of the front cap 50 and having a power supply terminal 64 disposed at one side thereof; and a rear housing 70 joined to the rear of the outer housing 3 for relaying supply of electric current, air and water from the outside.

The outer housing 3 is formed in a bar shape opened at the front and the rear and is capable of being grasped by the hand.

In this instance, the outer housing 3 has a diameter of a central circumference smaller than those of the front circumference and the rear circumference, and includes a plurality of protrusions formed on the outer circumferential surface of the rear of the outer housing 3, such that the user can stably grasp the outer housing 3 with the hand.

The cylindrical core 10 is inserted into the outer housing 3 and perforated from the front to the rear and includes: a coil 12 wound on the inner circumferential surface thereof from the front portion to the rear portion; and the air hole 14 and the water hole 16 perforated from one side of the front portion to one side of the rear portion.

In this instance, it is preferable that the core 10 have a pair of the air hole 14 and the water hole 16 perforated from one side of the front portion to one side of the rear portion, but a plurality of the air holes 14 and a plurality of the water holes 16 may be formed according to temperature of heat generated when the core 10 and the rotor 30 are operated.

The cylindrical pipes 20 are respective inserted into the air hole 14 and the water hole 16 of the core 10 in such a manner that both ends are protrudingly inserted into the front portion and the rear portion of the core 10, and are penetrated to pass air and water therethrough so as to relay the air and water supplied from the rear housing 70 to the front.

In this instance, a plurality of the pipes 20 are disposed according to the number of the air holes 14 and the water holes 16 formed in the core 10 and transfer cold air of the air and water moving inside the pipes 20 whose outer circumferential surfaces are in contact with the inner circumferential surfaces of the air hole 14 and the water hole 16 of the core 10, so as to directly cool the heat, which is generated when the core 10 and the rotor 30 are operated, with the cold air of the air and water moving inside the pipes 20.

Additionally, because the pipes 20 are inserted into the air hole 14 and the water hole 16 of the core 10, they can secure wider spaces than the pipes disposed on the outer face of the core 10, and due to the secured space, the handpiece 2 becomes small-sized and slim and can effectively cool the heat generated when the core 10 and the rotor 30 are operated.

The rotor 30 is inserted into the core 10 and made with a cylindrical magnetic material and has the transfer shafts 32 respectively extending to the front and the rear.

In this instance, it is preferable that the rotor 30 be spaced apart from the inner circumferential surface of the core and be operated at about 50,000 rpm when receiving power supply. When the rotor 30 and the core 10 are operated at less than 50,000 rpm, the user cannot smoothly cut the teeth when cutting the teeth using the handpiece 2. However, when the rotor 30 and the core 10 are operated at more than 50,000 rpm, the rotor 30 and the core 10 are damaged or broken due to excessive heat of the rotor 30 and the core 10.

The cylindrical support rings 34 are respectively forcedly fit to both sides of the transfer shafts 32 of the rotor 30 in such a manner that one side of each support ring 34 toward the rotor 30 comes in contact with the rotor 30 and the other side is formed protrudingly.

In this instance, the support rings 34 are respectively penetrated from the front to the rear such that they are respectively forcedly fit to the transfer shafts 32, and the protruding sides of the support rings 34 disposed in the opposite direction of the rotor 30 are respectively fixed to the inner rings of the bearings 36 which are toward the rotor 30 in a state where the protruding sides are in contact with sides of the inner rings of the bearings 36.

Moreover, the support rings 34 are made of synthetic resin or a metallic material and surround the outside of the transfer shafts 32 so as to prevent vibration generated when the transfer shafts 32 are rotated and increase a structural intensity of the transfer shafts 32, and thus, prevent transformation of the transfer shafts 32 even though power exceeding allowable stress is applied to the transfer shafts 32.

The bearings 36 are respectively disposed at the front side and the rear side of the support rings 34 and forcedly fit to the transfer shafts 32 so as to rotatably support the rotor 30.

In this instance, the bearings 36 are respectively fit to the front portion and the rear portion of the rotor 30 in such a way as to surround the outside of the transfer shafts 32 so as to prevent vibration generated when the transfer shafts 32 are rotated and increase a structural intensity of the transfer shafts 32, and thus, prevent transformation of the transfer shafts 32 even though power exceeding allowable stress is applied to the transfer shafts 32.

The coupling 38 is disposed in front of the rotor 30 and joined to the shaft 32.

In this instance, a shaft (not shown) and a worm gear (not shown) are connected to the front side of the coupling 38 in order so as to rotatably operate a drill of the handpiece 2.

The front housing 40 is joined to the front of the outer housing 3, includes an air jet hole 42 and a water jet hole 44 respectively formed in the outer circumference thereof for jetting air and water supplied from the pipes 20, and is penetrated from the front to the rear such that the transfer shafts 32 and the coupling 38 are inserted into the front housing 40.

In this instance, it is preferable that the front housing 40 have the air jet hole 42 and the water jet hole 44, but the number of the air jet hole 42 and the water jet hole 44 may be varied according to the number of the pipes 20.

The front cap 50 is disposed at the rear of the core 10, and includes a recess 52 opened toward the front such that the bearing 36 located at the rear of the rotor 30 is inserted into the recess 52 and a plurality of through holes 54 penetrated from the front to the rear and spaced apart from the recess 52.

In this instance, the front cap 50 is inserted into the rear portion of the outer housing 3, and the power supply terminal 64 which is connected with the pipes 20 and the core 10 for supplying electric current is joined to the front cap 50 and protrudes backwardly.

The rear cap 60 is disposed at the rear of the front cap 50, and includes: a plurality of through holes 62 formed from the front to the rear corresponding to the through holes 54 of the front cap 50; and the power supply terminal 64 spaced apart from the through holes 62 and disposed at one side thereof for supplying electric current to the core 10.

In this instance, as described above, the power supply terminal 64 of the rear cap 60 is connected with the core 10 so as to supply the electric current received from the outside, and the pipes 20 protruding through the through holes 54 of the front cap 50 are joined to the plural through holes 62 in such a way as to protrude backwardly.

Furthermore, it is preferable that outer circumferences of the through holes 62 formed in the rear cap 60 be opened such that pipe fixing members 22 which will be described later can be easily attached and detached.

The pipe fixing members 22 are formed in a cylindrical shape and made of synthetic resin. The pipe fixing members 22 are respectively joined to the through holes 62 of the rear cap 60 and joined to the rear portions of the pipes 20 so as to prevent separation of the pipes 20.

In this instance, the pipe fixing members 22 surround the outer faces of the pipes 20 so as to prevent movement and damage of the pipes 20, and thus, prevent a leakage of air and water flowing in through the rear housing 70.

The rear housing 70 is joined to the rear of the outer housing 3 for relaying supply of electric current, air and water from the outside.

In this instance, a connector (not shown) having a power supply and supply hoses is connected to the rear housing 70. The connector may be one of conventionally used connectors or one of other new connectors.

As described above, because the pipes 20 for making flow in air and water are joined to the air hole 14 and the water hole 16 of the core 10, heat generated when the handpiece 2 is operated is effectively cooled by the pipes 20, and thus, the handpiece 2 with the slim driving part of the direct cooling type according to the preferred embodiment of the present invention can prevent reduction of the lifespan of the handpiece and generation of vibration and noise due to overheating of the handpiece 2. Moreover, compared with the conventional handpiece having the pipes disposed on the outer face of the core 10, the handpiece having the pipes inserted into the air hole 14 and the water hole 16 of the core 10 according to the preferred embodiment of the present invention can secure a wider space and become small-sized and slim due to the secured space.

What is claimed is:

1. A handpiece with a slim driving part of a direct cooling type, the handpiece comprising:
    an outer housing formed in a bar shape and including a first penetrating hole extending from a front end of the outer housing to a rear end of the outer housing;
    a cylindrical core inserted into the first penetrating hole of the outer housing, the cylindrical core including
        a second penetrating hole extending from a front end of the cylindrical core to a rear end of the cylindrical core,
        a coil wound on an inner circumferential surface of the cylindrical core such that an outer circumferential surface of the cylindrical core is free from the coil, and
        an air hole and a water hole formed between the inner circumferential surface and the outer circumferential surface of the cylindrical core and extending from the front end of the cylindrical core to the rear end of the cylindrical core;
    a pair of cylindrical pipes
        inserted into the air hole and the water hole of the cylindrical core, respectively, so that both ends of the cylindrical pipes are protruded from the air hole and the water hole of the cylindrical core and
        configured to pass air and water, respectively, to cool the cylindrical core;
    a cylindrical rotor of a magnetic material and inserted into the second penetrating hole of the cylindrical core, the cylindrical rotor including a transfer shaft;
    front and rear cylindrical support rings coupled to a front portion and a rear portion of the transfer shaft of the rotor, respectively;
    front and rear bearings coupled to the front portion and the rear portion of the transfer shaft, respectively, so as to rotatably support the cylindrical rotor;
    a coupling coupled to the front portion of the transfer shaft, wherein the coupling is arranged forward of the front bearing, the front bearing is arranged forward of the front cylindrical support ring, and the rear cylindrical support ring is arranged forward of the rear bearing;
    a front housing including
        a third penetrating hole extending from a front end of the front housing to a rear end of the front housing, and
        an air jet hole and a water jet hole formed on an outer surface of the front housing and extended to the rear end of the front housing,
        wherein
            the front housing is coupled to the front end of the outer housing and the pair of cylindrical pipes, such that the transfer shaft and the coupling are inserted into the third penetrating hole of the front housing, and
            the air jet hole and the water jet hole are coupled to the pair of cylindrical pipes so as to jet air and water supplied from the pair of cylindrical pipes;
    a front cap coupled to the rear end of the cylindrical core, the front cap including:
        a recess opened toward a front side of the front cap such that the rear bearing coupled to the rear portion of the transfer shaft is inserted into the recess; and a plurality of front through holes extending from a front surface to a rear surface of the front cap and spaced apart from the recess;

a rear cap coupled to the rear surface of the front cap, the rear cap including:

a plurality of rear through holes extending from a front surface to a rear surface of the rear cap, and aligned with the plurality of front through holes of the front cap; and a power supply terminal spaced apart from the plurality of rear through holes and configured to supply electric current to the cylindrical core via the front cap coupled to the rear end of the cylindrical core;

pipe fixing members extending through the plurality of rear through holes and coupled to rear portions of the cylindrical pipes to prevent separation of the cylindrical pipes, each of the pipe fixing members having a cylindrical shape and comprising synthetic resin; and a rear housing
coupled to the rear end of the outer housing and
configured to relay electric current, air and water from outside, wherein
the outer housing comprises a central portion between the front end and the rear end of the outer housing, and
an outer diameter of the central portion is smaller than outer diameters of the front end and the rear end of the outer housing, wherein the power supply terminal is electrically connected with the cylindrical core and protruded to a front surface of the rear housing, and wherein outer circumferences of the plurality of rear through holes formed in the rear cap are partly opened.

* * * * *